United States Patent [19]

Higgs et al.

[11] Patent Number: 5,064,613
[45] Date of Patent: Nov. 12, 1991

[54] SOLID ANTIMICROBIAL

[75] Inventors: Bruce S. Higgs, Sydney, Australia; William C. White, Midland, Mich.

[73] Assignee: Dow Corning Corporation, Midland, Mich.

[21] Appl. No.: 431,415

[22] Filed: Nov. 3, 1989

[51] Int. Cl.[5] ............................................. C23F 11/14
[52] U.S. Cl. .................................... 422/16; 106/14.05; 106/14.15; 106/14.16; 252/389.31; 252/389.32; 252/400.3; 252/400.31; 422/18; 422/28; 422/37
[58] Field of Search .................. 422/16, 18, 28, 37; 106/14.05, 14.15, 14.16; 252/389.31, 389.32, 400.3, 400.31

[56] References Cited

U.S. PATENT DOCUMENTS

| | | | |
|---|---|---|---|
| 3,560,385 | 2/1971 | Roth | 252/49.6 |
| 3,730,701 | 5/1973 | Isquith et al. | 71/67 |
| 3,794,736 | 2/1974 | Abbott et al. | 424/78 |
| 3,817,739 | 6/1974 | Abbott et al. | 71/67 |
| 3,860,709 | 1/1975 | Abbott et al. | 424/184 |
| 3,865,728 | 2/1975 | Abbott et al. | 210/169 |
| 4,005,028 | 1/1977 | Heckert | 252/99 |
| 4,055,637 | 10/1977 | Voronkov et al. | 424/184 |
| 4,161,518 | 1/1979 | Wen et al. | 424/52 |
| 4,259,103 | 3/1981 | Malek et al. | 71/67 |
| 4,282,366 | 8/1981 | Eudy | 556/413 |
| 4,371,577 | 2/1983 | Sato et al. | 428/96 |
| 4,394,378 | 7/1983 | Klein | 424/184 |
| 4,406,892 | 9/1983 | Eudy | 424/184 |
| 4,467,013 | 8/1984 | Baldwin | 428/289 |
| 4,472,327 | 9/1984 | Neefe | 264/1.9 |
| 4,504,541 | 3/1985 | Yasuda et al. | 428/264 |
| 4,557,854 | 12/1985 | Plueddemann | 252/174 |
| 4,564,456 | 1/1986 | Homan | 210/698 |
| 4,567,039 | 1/1986 | Stadnick | 132/70 |
| 4,614,675 | 9/1986 | Ona et al. | 427/387 |
| 4,615,882 | 10/1986 | Stockel | 424/80 |
| 4,631,273 | 12/1986 | Blehm et al. | 514/29 |
| 4,631,297 | 12/1986 | Battice et al. | 521/78 |
| 4,682,992 | 7/1987 | Fuchs | 55/279 |
| 4,721,511 | 1/1988 | Kupits | 8/188 |
| 4,772,593 | 9/1988 | Whalen et al. | 514/63 |
| 4,781,974 | 11/1988 | Bouchette | 428/288 |
| 4,822,667 | 4/1989 | Goad et al. | 428/265 |
| 4,835,019 | 5/1989 | White et al. | 427/387 |
| 4,842,766 | 6/1989 | White et al. | 252/309 |
| 4,847,088 | 7/1989 | Blank . | |

FOREIGN PATENT DOCUMENTS

| | | |
|---|---|---|
| 1217004 | 4/1987 | Canada . |
| 8601457 | 1/1987 | PCT Int'l Appl. . |
| 1321616 | 7/1973 | United Kingdom . |
| 1386876 | 3/1975 | United Kingdom . |
| 1433303 | 4/1976 | United Kingdom . |

OTHER PUBLICATIONS

Applied Microbiology, vol. 24, No. 6, Dec. 1972, A. J. Isquith et al, "Surface Bonded Antimicrobial Activity of an Organosilicon Quaternary Ammonium Chloride".

Primary Examiner—Robert J. Warden
Assistant Examiner—Timothy M. McMahon
Attorney, Agent, or Firm—Jim L. DeCesare

[57] ABSTRACT

A method of treating surfaces in order to eliminate microbial growth by adding an antibacterially effective amount of an organosilicon quaternary ammonium silatrane compound to the surface in order to destroy bacteria and fungi. The preferred organosilicon quaternary ammonium silatrane compound has the formula

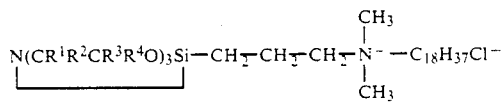

wherein $R^1$, $R^2$, $R^3$, and $R^4$, each represent a hydrogen atom or a methyl, ethyl, propyl, or butyl radical.

10 Claims, No Drawings

SOLID ANTIMICROBIAL

BACKGROUND OF THE INVENTION

This invention relates to a composition and to a method of treating surfaces with a solid form of an organic solvent borne antimicrobial agent in order to eliminate microbial growth.

An antimicrobial is an agent that destroys or inhibits the growth of microorganisms. The major classes of microorganisms are bacteria, fungi including mold and mildew, yeasts, and algae. Microorganisms can be found in the air, the waters, the human body, soil, wastes, and on all surfaces. The organisms are deposited from the air, food and drink spills, dust, dirt and tracked in soil, and from human excreta such as sweat, urine, and feces. Organisms grow and multiply when there is available a nutrient source of food such as dirt, organic or inorganic material, and living tissue. For growth and multiplication, organisms also require warm temperatures, and moisture. When these conditions exist, microorganisms thrive and flourish. Microbial growth, however, leads to many problems such as unpleasant odors ranging from stale to musty and mildew-like, to putrid and foul smelling, resembling ammonia. The growths also produce unsightly stains, discoloration, and deterioration of many surfaces and materials in which they come into contact. A more serious disadvantage of microbial growth is the production of pathogenic microorganisms, germs, their metabolic products and their somatic and reproductive cell parts, which contribute to the spread of disease, infection, and disorders.

Antimicrobial agents are chemical compositions that are used to prevent such microbiological contaminations by inhibiting, killing and/or removing them and neutralizing their effects of deterioration, defacement, odor, disease or other negative effects. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. In the area of medical applications, antimicrobials are often used as powders, in lotions, creams, ointments and/or delivered in a variety of solvents or directly as over-the-counter or ethical drugs to alleviate, mediate, cure and/or protect people or other animals from disease or cosmetic conditions. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone quaternary ammonium salt compounds are well known as exemplified by U.S. Pat. No. 3,560,385, issued Feb. 2, 1971, and the use of such compounds as antimicrobial agents is taught, for example, in a wide variety of patents such as U.S. Pat. Nos. 3,730,701, issued May 1, 1973, and 3,817,739, issued June 18, 1974, where the compounds are used to inhibit algae; 3,794,736, issued Feb. 26, 1974, and 3,860,709, issued Jan. 14, 1975, where they are employed for sterilizing or disinfecting a variety of surfaces and instruments; and 3,865,728, issued Feb. 11, 1975, where the compounds are used to treat aquarium filters. Published unexamined European Application No. 228464 of July 15, 1987, teaches that microorganisms on multi-cellular plants can be killed by the application thereto of an aqueous mixture of a surfactant and an organosilicon quaternary ammonium compound. U.S. Pat. No. 4,564,456, issued Jan. 14, 1986, discloses organosilanes as anti-scale agents in water systems. In a particular application of an antimicrobial silicone quaternary ammonium compound, a paper substrate is rendered resistant to the growth of microorganisms in U.S. Pat. No. 4,282,366, issued Aug. 4, 1981. In U.S. Pat. No. 4,504,541, issued Mar. 12, 1985, an antimicrobial fabric is disclosed which is resistant to discoloration and yellowing by treatment of the fabric with a quaternary ammonium base containing an organosilicone. U.S. Pat. No. 4,615,937, issued Oct. 7, 1986, as well as its companion U.S. Pat. No. 4,692,374, issued Sept. 8, 1987, relate to wet wiper towelettes having an antimicrobial agent substantive to the fibers of the web and being an organosilicon quaternary ammonium compound. In a series of Burlington Industries, Inc. U.S. Pat. Nos. 4,408,996, issued Oct. 11, 1983, 4,414,268, issued Nov. 8, 1983, 4,425,372, issued Jan. 10, 1984, and 4,395,454, issued July 26, 1983, such compounds are disclosed to be useful in surgical drapes, dressings, and bandages. This same assignee also discloses these compounds as being employed in surgeons' gowns in U.S. Pat. Nos. 4,411,928, issued Oct. 25, 1983, and 4,467,013, issued Aug. 21, 1984. Organosilicon quaternary ammonium compounds have been employed in carpets, in U.S. Pat. No. 4,371,577, issued Feb. 1, 1983; applied to walls, added to paints, and sprayed into shoes, in U.S. Pat. No. 4,394,378, issued July 19, 1983; formulated as aqueous emulsions in U.S. Pat. No. 4,631,273, issued Dec. 23, 1986; applied to polyethylene surfaces and used in pillow ticking in U.S. Pat. No. 4,721,511, issued Jan. 26, 1988; in flexible polyurethane foams of fine-called, soft, resilient articles of manufacture in U.S. Pat. No. 4,631,297, issued Dec. 23, 1986; and mixed with a surfactant in British Patent No. 1,386,876, of Mar. 12, 1975, and in Japanese Kokai Application No. 58-156809, filed Aug. 26, 1983, of Sanyo Chemical Industries, Ltd. Some general, more domestic type applications of these compounds, has included their use in a dentifrice as in U.S. Pat. No. 4,161,518 issued July 17, 1979; in a novel laundry detergent in U.S. Pat. No. 4,557,854, issued Dec. 10, 1985; as a hair conditioner in U.S. Pat. No. 4,567,039, issued Jan. 28, 1986; and in a soft contact lens disinfectant solution in U.S. Pat. No. 4,615,882, issued Oct. 7, 1986. In U.S. Pat. No. 4,614,675, issued Sept. 30, 1986, properties can be influenced by mixing the silicone quaternary ammonium salt compounds with certain siloxanes.

Other typical uses of organosilicon quaternary ammonium compounds in accordance with the prior art can be seen from U.S. Pat. Nos. 4,005,024; '025; '028; and '030; each issued on Jan. 25, 1977, and relating to hard surface rinse aids and detergents for hard surfaces. Contact lenses are treated with an organosilane in U.S. Pat. No. 4,472,327, issued Sept. 18, 1984. In U.S. Pat. No. 4,682,992, issued July 28, 1987, glass spheres are treated with the compounds and employed as filters. The compounds are used to treat swine dysentery in U.S. Pat. No. 4,772,593, issued Sept. 20, 1988; in a wet wiper in U.S. Pat. No. 4,781,974, issued Nov. 1, 1988; applied to a polyester fabric in U.S. Pat. No. 4,822,667, filed Apr. 18, 1989; and adhered to polyamide yarn in U.S. Pat. No. 4,835,019, issued May 30, 1989. In Canadian Patent No. 1,217,004, granted Jan. 27, 1987, organosilane quaternary ammonium compounds are formulated into bleaches that are applied to hard surfaces such as bath tubs, wash basins, toilets, drains, and ceramic tile floors.

The "unbound" antimicrobials of the prior art are not the equivalent of the "bound" antimicrobial organosilanes of the present invention because the unbound antimicrobials do not perform substantially the same function, in substantially the same way, to produce substantially the same results, as do the bound silanes of the present invention. The function differs because the bound antimicrobial is permanent whereas the unbound types are easily washed away or rubbed from the surface. The compounds of the present invention are not only durable but retain their antimicrobial activity after some ten laundering cycles, and only slightly diminish in their activity after as many as twenty-five laundering cycles. The bound silanes of the present invention retain an effective kill level of microorganisms. The manner in which the bound silane functions differs from the unbound types, since the bound silane attaches itself to the surface to which it is applied, whereas the unbound types are mere coatings which are not substantive. This is significant since the silane antimicrobial will continue to prevent reinfestation, and enables one to utilize the intrinsic antimicrobial activity of the silane treated surface to kill transient microbes, long after the unbound types of antimicrobials have been depleted of their activity. Further, the bound silanes of the present invention destroy, reduce, and inhibit the growth and multiplication of bacteria, fungi, and other pathogenic microorganisms, by the disruption of cell membranes, a mechanism absent from conventional unbound antimicrobial materials. The results produced by the bound silanes is not the same as the results produced by the unbound types, since the bound silanes provide a prolonged antimicrobial activity and continue to kill and inhibit the proliferation of potentially destructive microorganisms, versus mere temporary and superficial protection offered by the unbound category of material.

Among the numerous attempts to alleviate the problems of microorganisms on surfaces have involved the use of soaps, detergents, and surface cleaners. The treatments, however, have for the most part included an unbound category of antimicrobial which is not actually bonded to the surface sought to be treated, and therefore is consumed by the microorganisms, with the result that the unbound antimicrobial is depleted and washed away during routine cleansing. As this diffusion continues, the concentration of the active ingredient becomes diluted below effective levels, with the result that the microorganisms sought to be inhibited, adapt and build up a tolerance, becoming immune to what was once an effective treatment dose. Such unbound diffusible antimicrobials have therefore been found to be limited in their ability to offer broad spectrum control of microorganisms, in contrast to the bound type of antimicrobial which remains chemically attached to the surface to which it is applied providing for a surface that prevents recolonization by the microflora associated therewith. Diffusing types of antimicrobials also often suffer from the propensity to transfer percutaneously, giving rise to sensitization and irritation immunological responses, and raising serious questions as to their ultimate fate within the body and body systems.

Bound antimicrobials kill organisms on contact and continue to kill organisms without being diffused or leached from the surface. Thus, the bound antimicrobial leaves behind an effective level of active ingredient and is able to control a broad spectrum of microorganisms including gram negative and gram positive bacteria, mold, mildew, fungi, yeast, and algae. The compounds of the present invention have been found to be more effective at reducing the number of microorganisms, and inhibiting microbially generated odors, than conventional organotin compounds and other organic quaternary ammonium compounds. The silanes of the present invention when delivered from simple water solutions immobilize on surfaces and bond thereto to provide a coating of immobilized antimicrobial, unlike conventional materials.

The class of organofunctional silane antimicrobials referred to above are compounds whose methoxy, ethoxy, propoxy and butoxy silanes are stabilized by their corresponding solvents. To maximize the stability of these compounds, the solvents must be present. Disadvantages of this are, but not limited to, associated toxicities, odors, flammability, and difficulties in formulating with other useful materials.

In the present invention, this bound characteristic of organic solvent borne organosilicon quaternary ammonium compounds is maintained when water delivered, as well as their capabilities of performing at effective kill levels beyond prior art types of compositions, is taken advantage of in the treatment of surfaces, in order to reduce or substantially eliminate the incidence of microorganisms, germs, their metabolic products and their somatic and reproductive cell parts, which contribute to the spread of such microbes and the problems they cause such as deterioration, defacement, odors, and health problems of plants and animals. All of this is accomplished from the easily derived solid forms represented by the silatranes, eliminating the need for solvents and the associated problems of solvents.

Organosilicon compounds containing silatrane groups are not new. For example, United Kingdon Patent No. 1,321,616, granted June 27, 1973, shows such compounds and discloses the silatrane compositions to possess the utility of a surface active agent. In U.S. Pat. No. 4,055,637, issued Oct. 25, 1977, 1-chloromethylsilatrane is disclosed to be useful as a medicinal preparation for healing wounds and treating dermatities. However, the prior art does not show bound type antimicrobially active quaternary ammonium type organosilicon silatrane compounds as provided by the present invention.

SUMMARY OF THE INVENTION

This invention relates to a method of treating a surface harboring microorganisms in order to combat the microorganisms by destroying the microorganisms or by preventing proliferation of the microorganisms to numbers that would be destructive to the surface sought to be treated and protected, or whose body parts or metabolic products can give rise to odors, defacement, or negatively affect other life forms. The method includes reacting an alkanolamine with an organosilicon quaternary ammonium compound to form a silatrane compound in the form of a solid particulate powder, dissolving the silatrane powder in an aqueous medium to form an antimicrobially active solution of the silatrane powder, and applying the solution in an antimicrobially effective amount to the surface sought to be treated and protected, the organosilicon quaternary ammonium compound being an organosilane having the formula selected from the group consisting of

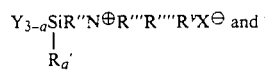

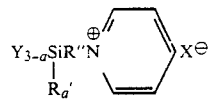

wherein, in each formula,
Y is R or RO where each R is an alkyl radical of 1 to 4 carbon atoms or hydrogen;
a has a value of 0, 1 or 2;
R' is a methyl or ethyl radical;
R'' is an alkylene group of 1 to 4 carbon atoms;
R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; and
X is chloride, bromide, fluoride, iodide, acetate or tosylate.

The treatment can be applied in the form of an emulsion including water, the silatrane, and a water immiscible liquid which is a polysiloxane selected from the group consisting of polysiloxanes having the general formula $R'_3SiO(R''_2SiO)_w(R'''QSiO)_zSiR'_{p3}$ and $(R'R''SiO)_y$ wherein R' is an alkyl radical of 1 to 3 carbon atoms, phenyl, an alkoxy radical having the formula R''''O—, wherein R'''' is an alkyl radical of 1 to 4 carbon atoms or hydrogen; R'' is an alkyl radical of 1 or 2 carbon atoms or the phenyl group; R''' has the same meaning as R''; Q is a substituted or unsubstituted radical composed of carbon and hydrogen, or carbon, hydrogen and oxygen, or carbon, hydrogen and sulfur, or carbon, hydrogen and nitrogen; w has a value of from 1 to 500; z has a value of 1 to 25 and y has a value of 3 to 5.

The most preferred organosilane quaternary ammonium compound for use in preparing the silatranes in accordance with the method of the present invention is 3-(trimethoxysilyl) propyldimethyloctadecyl ammonium chloride (TMS) of the formula

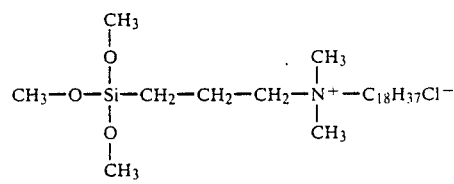

The invention is also directed to compounds prepared in accordance with the above described method.

These and other features, objects, and advantages, of the present invention will be apparent when considered in light of the following detailed description thereof.

DETAILED DESCRIPTION OF THE INVENTION

Ammonium compounds in which all of the hydrogen atoms on nitrogen have been substituted by alkyl groups are called quaternary ammonium salts. These compounds may be represented in a general sense by the formula:

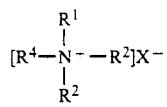

The nitrogen atom includes four covalently bonded substituents that provide a cationic charge. The R groups can be any organic substituent that provides for a carbon and nitrogen bond with similar and dissimilar R groups. The counterion X is typically halogen. Use of quaternary ammonium compounds is based on the hydrophilic portion of the molecule which bears a positive charge. Since most surfaces are negatively charged, solutions of these cationic surface active agents are readily adsorbed to the negatively charged surface. This affinity for negatively charged surfaces is exhibited by a compound hereinafter referred to as "TMS" which is 3-(trimethoxysilyl)propyldimethyloctadecyl ammonium chloride of the formula:

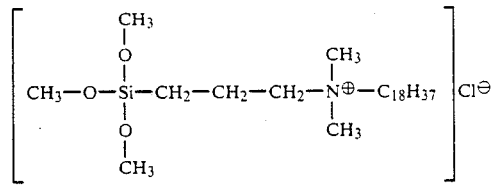

In the presence of moisture, this antimicrobial agent imparts a durable, wash resistant, broad spectrum biostatic surface antimicrobial finish to a substrate. The organosilicon quaternary ammonium compound is leach resistant, nonmigrating, and is not consumed by microorganisms. It is effective against gram positive and gram negative bacteria, fungi algae, yeasts, mold, rot, and mildew. The silicone quaternary ammonium complex provides durable, bacteriostatic, fungistatic, and algistatic surfaces.

The silanes useful in preparing the silatranes in accordance with this invention have the general formula

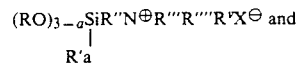

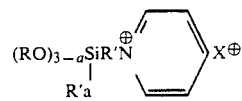

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R. Malek and John L. Speier, on Mar. 31, 1981, discusses the use of such silanes to render the surfaces of certain substrates antimicrobial. British Patent No. 1,433,303, issued to Charles A. Roth shows the use of fillers treated with certain silanes to be used in paints and the like to give antimicrobial effects.

Numerous other publications have disclosed such silanes, namely, A. J. Isquith, E. A. Abbott and P. A. Walters, Applied Microbiology, December 1972, pages 859-863; P. A. Walters, E. A. Abbott and A. J. Isquith, Applied Microbiology, 25, No. 2, p. 253-256, February 1973 and E. A. Abbott and A. J. Isquith, U.S. Pat. No. 3,794,736 issued Feb. 26, 1974, U.S. Pat. No. 4,406,892, issued Sept. 27, 1983, among others.

For purposes of this invention, the silanes can be used neat or they can be used in solvent or aqueous-solvent solutions. When the silanes are used neat, the inventive process is preferably carried out in a system in which some small amount of water is present. If it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the $\equiv$SiOH that is formed by the hydrolysis of the alkoxy groups present on the silane. The $\equiv$SiOH groups tend to react with the surface and bind the silanes to the surface. It is believed by the inventor that even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radical. In the above formula RO can also be R. T can also be hydrogen thus indicating the silanol form, i.e. the hydrolyzate. The value of a is 0, 1 or 2 and R' is a methyl or ethyl radical. Because of the presence of these alkyl radicals, the prior art teaches that these materials must be stabilized with a corresponding solvent. Thus, methoxy groups require methanol and ethoxy groups require ethanol, for example.

R" for purposes of this invention is an alkylene group of 1 to 4 carbon atoms. Thus, R" can be alkylene groups such as methylene, ethylene, propylene, and butylene. R''', R'''', and $R^v$ are each independently selected from a group which consists of alkyl radicals of 1 to 18 carbons, $-CH_2C_6H_5$, $-CH_2CH_2OH$, $-CH_2OH$, and $-(CH_2)_xNHC(O)R^{vi}$. x has a value of from 2 to 10 and $R^{vi}$ is a perfluoroalkyl radical having from 1 to 12 carbon atoms. X is chloride, bromide, fluoride, iodide, acetate or tosylate.

Preferred for this invention are the silanes of the general formula

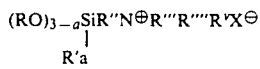

R is methyl or ethyl; a has a value of zero; R" is propylene; R''' is methyl or ethyl; R'''' and $R^v$ are selected from alkyl groups containing 1 to 18 carbon atoms wherein at least one such group is larger than eight carbon atoms and x is either chloride, acetate or tosylate.

As indicated above, most of these silanes are known from the literature and methods for their preparation are known as well. See, for example, U.S. Pat. No. 4,282,366, issued Aug. 4, 1981; U.S. Pat. No. 4,394,378, issued July 19, 1983, and U.S. Pat. No. 3,661,963 issued May 9, 1972, among others.

Specific silanes within the scope of the invention are represented by the formulae:

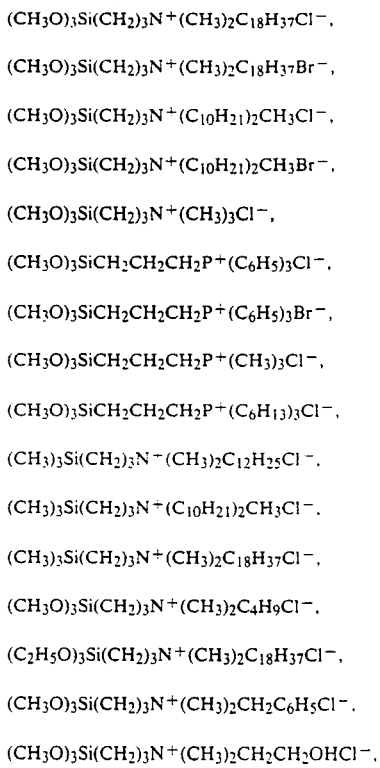

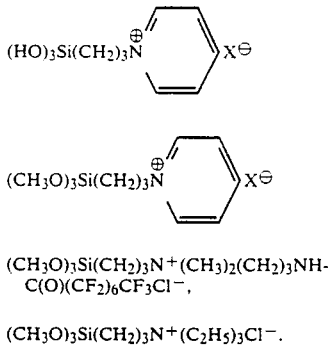

$(CH_3O)_3Si(CH_2)_3N^+(CH_3)_2(CH_2)_3NH-C(O)(CF_2)_6CF_3Cl^-$, $(CH_3O)_3Si(CH_2)_3N^+(C_2H_5)_3Cl^-$.

The water immiscible liquids, or volatiles as used in the emulsions of the present invention, are silicone oils which are highly volatile, and low in viscosity and molecular weight. For example, there may be employed trimethylsiloxy endblocked polydimethylsiloxanes, cyclic siloxanes such as dimethylsiloxane cyclic tetramer, and phenylmethyl fluids such as linear polyphenylmethylsiloxanes. Preferred for this invention are those silicone oils having a viscosity at twenty-five degrees Centigrade ranging from about 0.65 cs to about one thousand cs. A particularly preferred range is from about 0.65 cs to about 20 cs, although those silicone oils of viscosities of 50 cs, and 350 cs, can be employed. These silicone oils are more particularly described and set forth in detail in U.S. Pat. No. 4,631,273, issued Dec. 23, 1986, the disclosure of which is incorporated herein by reference. Such silicone oils are siloxanes which are low molecular weight cyclics and polysiloxanes having the general formula R'$_3$SiO(R''$_2$SiO)$_w$(R'''QSiO)$_z$SiR'$_3$ and (R'R''SiO)$_y$ wherein R' is an alkyl radical of 1 to 3 carbon atoms, phenyl, an alkoxy radical having the formula R''''O—, wherein R'''' is an alkyl radical of 1 to 4 carbon atoms or hydrogen; R'' is an alkyl radical of 1 or 2 carbon atoms or the phenyl group; R''' has the same meaning as R''; Q is a substituted or unsubstituted radical composed of carbon and hydrogen, or carbon, hydrogen and oxygen, or carbon, hydrogen and sulfur, or carbon, hydrogen and nitrogen; w has a value of from 1 to 500; z has a value of 1 to 25 and y has a value of 3 to 5.

The organosilane silatrane may also be employed in accordance with the present invention in the form of a microemulsion containing the silatrane. Such microemulsions and their preparation are described in applicants' prior copending application U.S. Ser. No. 07/015,645, filed Feb. 17, 1987, now U.S. Pat. No. 4,842,766 issued June 27, 1989, and assigned to the same assignee as the present application. Solutions with particle sizes less than 0.150 microns are disclosed which are either oil-in-water or water-in-oil microemulsions including the silatrane and at least one surfactant. The prior copending application relating to the microemulsions is considered incorporated herein by reference, as is U.S. Pat. No. 4,631,273, issued Dec. 23, 1986, relating to the formation of emulsions including the silatranes of the present invention. The '273 patent is also assigned to the same assignee as the present application.

Various procedures are employed in order to test the organosilanes of the present invention. For example, the presence of the chemical on a substrate can be determined by complexing a standardized solution of bromophenol blue in water with the quaternary nitrogen of the organosilane and recording the color change spectrophotometrically. Results of this test can be used in order to determine whether the organosilane has bound itself to a particular surface. Such a test procedure is set forth below.

The anion of an aqueous sodium salt of bromphenol blue can be complexed with the cation of polymerized silanes of this invention while on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

One method consists of preparing a 0.02 to 0.04 weight percent solution of bromphenol blue in distilled water. This solution is made alkaline using a few drops of saturated Na$_2$CO$_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used. The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated Na$_2$CO$_3$ solution per 100 milliliters of bromphenol blue solution. The color of this solution is purple. The blank solution is adjusted to yield a 10 to 12% transmittance reading when measured in 1 cm cells using a spectrophotometer set at 589 nm by the following method. Fill a container ¾ full of distilled water and add 2 ml of the 0.02% standard bromphenol blue solution for every 50 ml of distilled water. Add 0.5 ml of a 1% Triton® X-100 surfactant (manufactured by Rohm and Haas, Philadelphia, PA, USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate can be tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted.

The antimicrobial activity of a treated surface is normally evaluated by shaking a sample weighing 0.75 grams in a 750,000 to 1,500,000 count *Klebsiella pneumoniae* suspension for a one hour contact time. The suspension is serially diluted, both before and after contact, and cultured. The number of viable organisms in the suspensions is determined. The percent reduction based on the original count is determined. The method is intended for those surfaces having a reduction capability of 75 to 100% for the specified contact time. The results are reported as the percent reduction. Media used in this test are nutrient broth, catalog No. 0003-01-6 and tryptone glucose extract agar, catalog No. 0002-01-7 both available from Difco Laboratories, Detroit, Mich. U.S.A. The microorganism used is *Klebsiella pneumoniae* American Type Culture Collection; Rockville, Md. U.S.A., catalog No. 4352. The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer. The tubes are agitated with a vortex mixer and then 1 ml of each solution is transferred to a second test tube containing 9 ml of sterile buffer. Then, after agitation of the tubes, 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the $10^0$ and $10^{-1}$ dilutions as well as at the $10^{-2}$ dilution. "Percent reduction" is calculated by the formula $$\% R = \frac{\frac{B+C}{2} - A}{\frac{B+C}{2}} 100$$

where A is the count per milliliter for the flask containing the treated substrate; B is zero contact time count per milliliter for the flask used to determine "A" before the addition of the treated substrate and C is zero contact time count per milliliter for the untreated control substrate.

The foregoing "Shake Flask Test" measures antimicrobial substrate activity. An alternative test sometimes employed is the "Agar Plate Graphing Technique" which again affords a measure of antimicrobial substrate activity, in which treated swatches of fabric are placed on agar impregnated with *Klebsiella pneumoniae*. Antimicrobial activity is measured by the existence of a zone of inhibition and diffusability in the agar. Immobilized antimicrobials will not show a zone.

It is also possible to measure antimicrobial solution activity and this is performed in accordance with the procedures of the "Minimum Inhibitory Concentration Test(MIC)" in which the level of chemical required to inhibit the growth of microorganisms in a system is determined, typically employing organisms such as *Staphylococcus aureus*, *Klebsiella pneumoniae*, and *Aspergillus niger*.

The following examples illustrate the concepts of the present invention.

EXAMPLE I

A white powder antimicrobial solid was prepared by the reaction of 118.9 grams of 3-(trimethoxysilyl) propyldimethyl octadecyl ammonium chloride and 142 grams of methanol with 14.9 grams of triethanolamine in a solvent mixture of 9 grams isobutanol and 50 grams of toluene. These materials were heated and refluxed with stirring. Over a period of three hours, the methanol solvents and water were distilled off and the mixture cooled. A white solid representing 84% of theoretical yield was obtained after vacuum filtration.

While the foregoing example employs triethanolamine as a reactant to produce the silatrane reaction product, any alkanolamine is appropriate.

EXAMPLE II

The Shake Flask antimicrobial test explained above was employed in order to determine antimicrobial activity. Cotton fabric was treated with one percent by weight of the white powder in a water solution. Both ten and thirty minute soaks provided a reduction of 100 percent in comparison to a reduction of 64.8 percent for a control, indicating excellent antimicrobial activity for the organosilane silatrane composition of the present invention.

EXAMPLE III

There was heated and stirred for three hours a mixture including 118.4 grams of 3-(trimethyloxysilyl) propyldimethyloctadecyl ammonium chloride. 141 grams of methanol, 14.9 grams of triethanolamine, and fifty grams of toluene. The mixture was dried in a forced air oven at about two-hundred degrees Centigrade to yield a yellow-white powder. The powder was washed three times with acetone resulting in a dry white powder material.

A ladder series of concentration calculated as fully hydrolyzed 3-trioxysilylpropyl dimethyloctadecyl ammonium chloride were prepared using the triethanolamine silatrane of 3-trimethoxysilylpropyl dimethyloctadecyl ammonium chloride (I) and 3-trimethyoxysilylpropyl dimethyloctadecyl ammonium chloride (II), the ladder being composed of 0.09, 0.1., 0.25, 0.50 and 1.00% by weight active on cotton and polyester fabrics. Treatment was accomplished by wet weight pick up from tap water solutions of the test compounds. The fabrics were dried and tested by the following procedures:

A. Dynamic Shake Flask Antibacterial Test—*Klebsiella pneumonia* Gram (−) and *Staphylococcus Aureus* Gram (+). Standard procedure.
B. Bromophenolblue Spectrophotometric Analytical Test. 0.5 g test fabric used in standard procedure.
C. A above after 2 grams of the test fabric were rinsed in 200 ml of 40° C. deionized water for 20 minutes, squeezed dry and oven dryed at 100° C.
D. B above per C.
E. Zone of Inhibition
  1. Tryptocase Soy Agar, 1⅞" fabric circle placed on lawn of *Klebsiella pneumoniae* (24 hour broth culture diluted 1:100 in sterile deionized water phosphate buffer, 1 ml spread on plate as lawn) or *Staphylococcus aureus* (prepared as above). Readings after 48 hours incubation at 37° C.
  2. Saborauds Dextrose Agar, 1⅞" fabric circle placed on agar and innoculated with a spore suspension with Triton ® X-100 wetting agent of *Aspergillus niger*.

Readings were made for total coverage after 21 days incubation at 30° C.

F. Zone of Inhibition Run as E with samples per C.
The test results are shown in the Tables that follow.

The evidence of a leaching component that gives a zone of inhibition is clear from tests E and F showing a zone before rinse and no zone after rinse and from tests A and C where the activity against the test organisms is measurably reduced after rinsing. The durability of the antimicrobial as the silane quaternary amine as the monomer or as delivered from the hydrolysis of the silatrane is seen clearly from tests E and F, surface growth of *A. niger* profile the same and tests B and D showing analytical equivalence from rinsed/nonrinsed silane/silatrane comparisons and tests A and C showing identical minimal activity profiles silane/silatrane.

The silatrane of triethanolamine and 3-trimethoxysilylpropyl dimethyloctadecyl ammonium chloride provides a water soluble solid delivery form of 3-trimethoxysilylpropyl dimethyloctadecyl ammonium chloride that provides a durable antimicrobial surface after a rinse protocol and provides for a leaching antimicrobial before rinsing. Upon contact with water, the silatrane reverts to TMS and triethanolamine.

TABLE I

Analytical and Antimicrobial Tests - Silatrane

| Sample | A. DSF-Antibacterial % Reduction | | B. BPB-Analytical % Transmission | C. DSF (Rinsed) % Reduction | | D. BPB (Rinsed) % Transmission |
|---|---|---|---|---|---|---|
| | K. pneumoniae | S. aureus | | K. pneumoniae | S. aureus | |
| Active Ingredient I. (Silatrane) | | | | | | |
| Fabric: Cotton | | | | | | |
| 0.00% | 16 | 32 | 11.0 | 19 | 26 | 11.0 |
| 0.10% | 46 | 64 | 12.5 | 38 | 42 | 12.5 |
| 0.25% | 98 | 100 | 21.0 | 94 | 84 | 23.0 |
| 0.50% | 99.99 | 100 | 58.0 | 99.9 | 99.9 | 73.0 |
| 1.00% | 100 | 100 | 68.0 | 100 | 100 | 81.0 |
| Fabric: Polyester | | | | | | |
| 0.00% | 0 | 3 | 11.0 | 0 | 4 | 11.0 |
| 0.10% | 28 | 35 | 12.0 | 41 | 28 | 13.0 |
| 0.25% | 92 | 100 | 27.0 | 86 | 96 | 36.0 |
| 0.50% | 97 | 100 | 61.0 | 93 | 100 | 64.0 |
| 1.00% | 100 | 100 | 75.0 | 100 | 100 | 78.0 |
| Analytical Blank | — | — | 11.0 | | | 11.0 |

| Sample | E. Zone of Inhibition mm | | | Surface Growth % Covered 21 Days | F. Zone of Inhibition (Rinsed) mm | | | Surface Growth % Covered 21 Days |
|---|---|---|---|---|---|---|---|---|
| | K. pneumoniae | S. aureus | A. niger | | K. pneumoniae | S. aureus | A. niger | |
| Active Ingredient I. (Silatrane) | | | | | | | | |
| Fabric: Cotton | | | | | | | | |
| 0.00% | 0 | 0 | 0 | 100 | 0 | 0 | 0 | 100 |
| 0.10% | 0 | 0 | 0 | 75 | 0 | 0 | 0 | 80 |
| 0.25% | 1 | 3 | 0 | 50 | 0 | 0 | 0 | 40 |
| 0.50% | 2 | 7 | 0 | 0 | 0 | 0 | 0 | 0 |
| 1.00% | 4 | 8 | 1 | 0 | 0 | 0 | 0 | 0 |
| Fabric: Polyester | | | | | | | | |
| 0.00% | 0 | 0 | 0 | 100 | 0 | 0 | 0 | 100 |
| 0.10% | 0 | 0 | 0 | 75 | 0 | 0 | 0 | 80 |
| 0.25% | 0 | 2 | 0 | 10 | 0 | 0 | 0 | 20 |
| 0.50% | 1 | 4 | 0 | 0 | 0 | 0 | 0 | 0 |
| 1.00% | 3 | 6 | 1 | 0 | 0 | 0 | 0 | 0 |
| Analytical Blank | — | — | — | — | — | — | — | — |

TABLE II

Analytical and Antimicrobial Tests: TMS

| Sample | A. DSF-Antibacterial % Reduction | | B. BPB-Analytical % Transmission | C. DSF (Rinsed) % Reduction | | D. BPB (Rinsed) % Transmission |
|---|---|---|---|---|---|---|
| | K. pneumoniae | S. aureus | | K. pneumoniae | S. aureus | |
| Active Ingredient II. TMS | | | | | | |
| Fabric: Cotton | | | | | | |
| 0.00% | 22 | 38 | 11.0 | 18 | 29 | 11.0 |
| 0.10% | 63 | 65 | 13.5 | 55 | 48 | 12.5 |
| 0.25% | 72 | 84 | 28.0 | 83 | 90 | 23.0 |
| 0.50% | 99.9 | 100 | 1.0 | 99.5 | 100 | 58.0 |
| 1.00% | 100 | 100 | 72.0 | 100 | 100 | 75.0 |
| Fabric: Polyester | | | | | | |
| 0.00% | 0 | 2 | 11.0 | 0 | 3 | 11.0 |
| 0.10% | 48 | 52 | 16.0 | 32 | 28 | 14.0 |
| 0.25% | 98 | 99.99 | 34.0 | 96 | 98.6 | 29.0 |
| 0.50% | 100 | 99.99 | 74.0 | 100 | 100 | 65.0 |
| 1.00% | 100 | 100 | 86.0 | 100 | 100 | 82.0 |
| Analytical Blank | — | — | 11.0 | | | 11.0 |

| Sample | E. Zone of Inhibition mm | | | Surface Growth % Covered | F. Zone of Inhibition (Rinsed) mm | | | Surface Growth % Covered |
|---|---|---|---|---|---|---|---|---|
| | K. pneumoniae | S. aureus | A. niger | | K. pneumoniae | S. aureus | A. niger | |

TABLE II-continued

Analytical and Antimicrobial Tests: TMS

| | mm | | | 21 Days | mm | | | 21 Days |
|---|---|---|---|---|---|---|---|---|
| Active Ingredient II. TMS | | | | | | | | |
| *Fabric: Cotton* | | | | | | | | |
| 0.00% | 0 | 0 | 0 | 100 | | | | 100 |
| 0.10% | 0 | 0 | 0 | 70 | 0 | 0 | 0 | 75 |
| 0.25% | 0 | 0 | 0 | 25 | 0 | 0 | 0 | 30 |
| 0.50% | 0 | 0 | 0 | 0 | 0 | 0 | 0 | 0 |
| 1.00% | 0 | 0 | 0 | 0 | 0 | 0 | 0 | 0 |
| *Fabric: Polyester* | | | | | | | | |
| 0.00% | 0 | 0 | 0 | 100 | 0 | 0 | 0 | 100 |
| 0.10% | 0 | 0 | 0 | 60 | 0 | 0 | 0 | 50 |
| 0.25% | 0 | 0 | 0 | 0 | 0 | 0 | 0 | 0 |
| 0.50% | 0 | 0 | 0 | 0 | 0 | 0 | 0 | 0 |
| 1.00% | 0 | 0 | 0 | 0 | 0 | 0 | 0 | 0 |
| Analytical Blank | — | — | — | — | — | — | — | — |

The organosilane quaternary ammonium silatrane compound produced in the foregoing examples is shown in the following formula

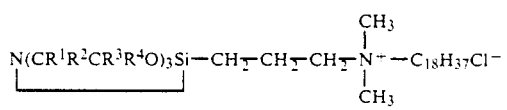

wherein $R^1$, $R^2$, $R^3$, and $R^4$, each represent a hydrogen atom or a methyl, ethyl, propyl, or butyl radical.

The genus of the organosilane silatrane compounds of the present invention is shown below, and in each formula, the radicals indicated therein are as previously defined above.

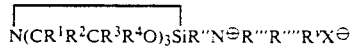

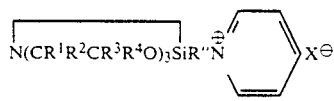

Regarding the activity of the compounds of the present invention, such compounds have been found to be effective against a number of microorganisms, such as "BACTERIA": Gram (−); *Escherichia coli, Klebsiella pneumoniae, Klebsiella oxytoca, Pseudomonas aeruginosa, Pseudomonas fluorescens, Proteus mirabilis, Proteus vulgaris, Salmonella typhi, Salmonella typhimurium, Salmonella cholera suis, Enterobacter cloacae, Enterobacter aerogenes, Morganella morganii, Aeromonas hydrophila, Citrobacter freundii, Citrobacter deversus, Serratia marcescens, Serratia liquifaciens, Xanthomonas campestris, Acinetobacter calcoaceticus*; Gram (+): *Staphylococcus aureus, Staphylococcus epidermidis, Streptococcus mutans, Streptococcus pyogenes, Streptococcus fecalis, Micrococcus lutea,* Bacillus sp. (vegetative cell); "Fungi": *Aspergillus niger, Aspergillus flavus, Aspergillus sydowi, Aspergillus versicolor, Aspergillus terreus, Penicillium chrysogenum, Penicillium variabile, Penicillium funiculosum, Penicillium pinophilum, Poria placenta, Aureobasidium pullulans, Gloeophyllum trabeum, Chaetomium globosum, Trichoderma viride, Trichophyton mentagrophytes;* "Fungi"(yeasts): *Candida albicans, Candida pseudotropicalis, Saccharomyces cerevisiae.*

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A method of treating a surface to combat microorganisms comprising reacting an alkanolamine with an organosilicon quaternary ammonium compound to form a solid particulate silatrane compound, dissolving the silatrane in an aqueous medium and forming an antimicrobially active solution of the silatrane, and applying the solution to the surface, the organosilicon quaternary ammonium compound being an organosilane having the formula selected from the group consisting of

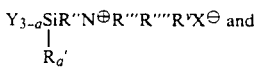 and

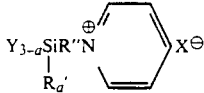

wherein, in each formula,

Y is R or RO where each R is an alkyl radical of 1 to 4 carbon atoms or hydrogen;

a has a value of 0, 1 or 2;

R' is a methyl or ethyl radical;

R'' is an alkylene group of 1 to 4 carbon atoms;

R''', R'''' and $R^v$ are each independently selected from a group consisting of alkyl radicals of 1 to 18 carbon atoms, —$CH_2C_6H_5$, —$CH_2CH_2OH$, —$CH_2OH$, and —$(CH_2)_xNHC(O)R^{vi}$, wherein x has a value of from 2 to 10 and $R^{vi}$ is a perfluoroalkyl radical having from 1 to 12 carbon atoms; and X is chloride, bromide, fluoride, iodide, acetate or tosylate.

2. A method as claimed in claim 1 wherein the organosilicon compound has the formula

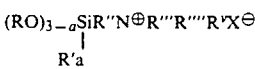

wherein each R is an alkyl radical of 1 to 4 carbon atoms or hydrogen; a has a value of 0, 1 or 2; R' is a methyl or ethyl radical; R" is an alkylene group of 1 to 4 carbon atoms; R''', R'''' and R$^v$ are each indenpendently selected from a group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; X is chloride, bromide, fluoride, iodide, acetate or tosylate.

3. A method as claimed in claim 1 wherein the organosilicon compound has the formula

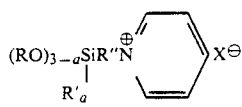

wherein R is an alkyl radical of 1 to 4 carbon atoms or hydrogen; a has a value of 0, 1 or 2; R' is a methyl or ethyl radical; R" is an alkylene of 1 to 4 carbon atoms; X is chloride, bromide, fluoride, iodide, acetate or tosylate.

4. The method of claim 1 wherein the organosilane is 3-(trimethoxysilyl) propyldimethyloctadecyl ammonium chloride of the formula

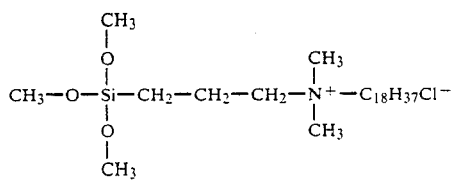

5. The method of claim 1 wherein the silatrane compound has the formula

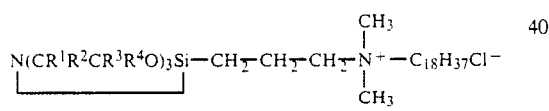

wherein R$^1$, R$^2$, R$^3$, and R$^4$, each represent a hydrogen atom or a methyl, ethyl, propyl, or butyl radical.

6. The method of claim 1 wherein the alkanolamine is triethanolamine.

7. A method of treating a surface to combat microorganisms comprising applying to the surface an aqueous solution of the compound

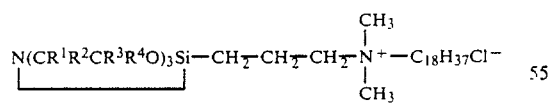

in which R$^1$, R$^2$, R$^3$ and R$^4$ each represent a hydrogen atom or a methyl, ethyl, propyl or butyl radical.

8. A method of treating a surface to combat microorganisms comprising applying to the surface an aqueous solution of a reaction product of an alkanolamine and an organosilicon quaternary ammonium compound having a formula selected from the group consisting of:

wherein in each formula
Y is R or RO where R is an alkyl radical of 1 to 4 carbon atoms or hydrogen;
a has a value of 0, 1 or 2;
R' is a methyl or ethyl radical;
R" is an alkylene group of 1 to 4 carbon atoms;
R''', R'''' and R$^v$ are each independently selected from the group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms; and
X is chloride, bromide, fluoride, iodide, acetate or tosylate.

9. A method of treating a surface to combat microorganisms comprising applying to the surface an aqueous solution of an alkanolamine silatrane of 3-trimethoxysilylpropyl dimethyloctadecyl ammonium chloride.

10. A method of treating a surface to combat microorganisms comprising applying to the surface an aqueous solution of a compound having a formula selected from the group consisting of:

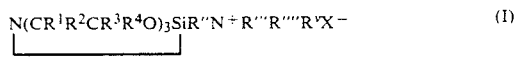

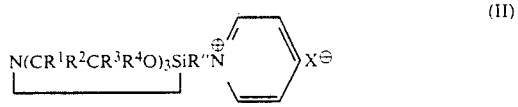

wherein in each formula
Y is R or RO where R is an alkyl radical of 1 to 4 carbon atoms or hydrogen;
a has a value of 0, 1 or 2;
R' is a methyl or ethyl radical;
R" is an alkylene group of 1 to 4 carbon atoms;
R''', R'''' and R$^v$ are each independently selected from the group consisting of alkyl radicals of 1 to 18 carbon atoms, —CH$_2$C$_6$H$_5$, —CH$_2$CH$_2$OH, —CH$_2$OH, and —(CH$_2$)$_x$NHC(O)R$^{vi}$, wherein x has a value of from 2 to 10 and R$^{vi}$ is a perfluoroalkyl radical having from 1 to 12 carbon atoms;
X is chloride, bromide, fluoride, iodide, acetate or tosylate; and
R$^1$, R$^2$, R$^3$ and R$^4$ each represent a hydrogen atom or a methyl, ethyl, propyl or butyl radical.

* * * * *